United States Patent
Raderman

(10) Patent No.: US 11,007,238 B2
(45) Date of Patent: *May 18, 2021

(54) CONCENTRATING CANNABINOIDS IN A LIPID SOLUTION USING MULTI-PHASE PRESSURE CYCLES

(71) Applicant: Raderman Holdings, LLC, Jamestown, CO (US)

(72) Inventor: Joshua Michael Raderman, Boulder, CO (US)

(73) Assignee: Raderman Holdings LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/777,811

(22) Filed: Jan. 30, 2020

(65) Prior Publication Data

US 2020/0164012 A1 May 28, 2020

Related U.S. Application Data

(60) Continuation of application No. 15/912,330, filed on Mar. 5, 2018, now Pat. No. 10,583,160, which is a division of application No. 15/260,607, filed on Sep. 9, 2016, now Pat. No. 9,937,219, and a continuation-in-part of application No. 15/043,604, filed on Feb. 14, 2016, now Pat. No. 9,867,859, which is a continuation of application No. 14/588,150, filed on Dec. 31, 2014, now Pat. No. 9,259,449.

(60) Provisional application No. 61/964,538, filed on Jan. 7, 2014.

(51) Int. Cl.
| | |
|---|---|
| *A61K 36/00* | (2006.01) |
| *A61K 36/185* | (2006.01) |
| *A61K 31/05* | (2006.01) |
| *A61K 47/44* | (2017.01) |
| *A61K 9/00* | (2006.01) |
| *A61K 9/48* | (2006.01) |

(52) U.S. Cl.
CPC .......... *A61K 36/185* (2013.01); *A61K 9/0014* (2013.01); *A61K 9/0053* (2013.01); *A61K 9/48* (2013.01); *A61K 31/05* (2013.01); *A61K 47/44* (2013.01); *A61K 2236/00* (2013.01); *A61K 2236/37* (2013.01); *A61K 2236/39* (2013.01); *A61K 2236/53* (2013.01); *A61K 2236/55* (2013.01)

(58) Field of Classification Search
CPC ..................................................... A61K 36/00
USPC ....................................................... 424/725
See application file for complete search history.

(56) References Cited

PUBLICATIONS

Prociuk et al., Canadian Journal of Physiology and Pharmacology (2008), 86(4), 153-159.*

* cited by examiner

*Primary Examiner* — Michael V Meller
(74) *Attorney, Agent, or Firm* — Kevin H. Fortin

(57) ABSTRACT

A concentrated lipid-based solution including tetrahydrocannabinol (THC) is manufactured by providing a lipid solution including an array of triglycerides, cannabinoids and water soluble contaminants in a pressure vessel. Water is added to the lipid solution to create a mixture and the pressure is increased in a first phase at a first pressure and duration and in a second phase at a second temperature and duration. The mixture is agitated to dissolve the water soluble contaminants. The mixture is cooled to cause the triglycerides and cannabinoids to solidify. The solidified triglycerides and cannabinoids, including THC, are separated to yield a purified cannabinoid solution.

1 Claim, 9 Drawing Sheets

104 →

Figure 1:
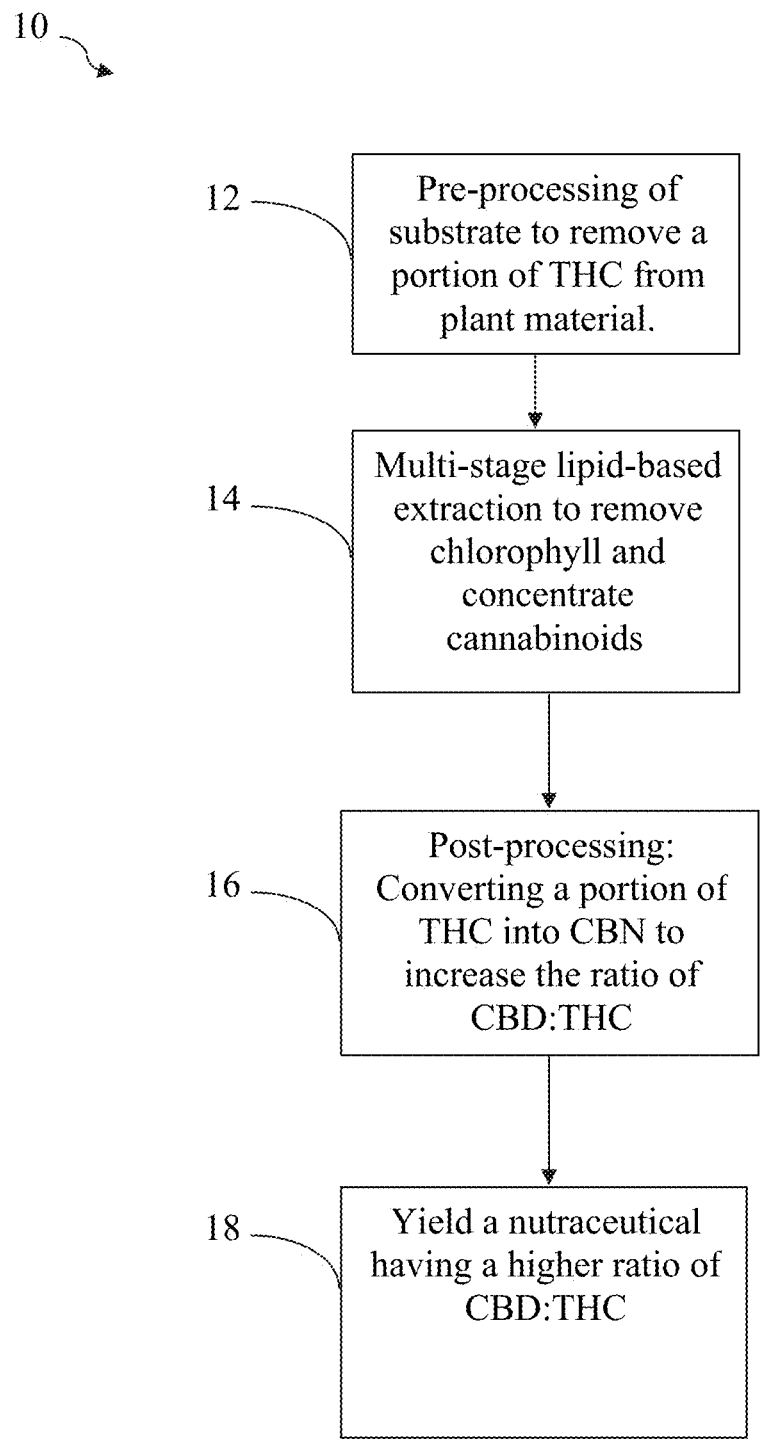

106 — Providing a lipid solution including triglycerides, cannabinoids, trace levels of contaminants, and a melting point of less than 40°C 108 — Adding purified water to create an aqueous mixture 110 — Heating the mixture in a pressure vessel to above the melting point and pressurizing beyond one atmosphere of pressure (ATM) to dissolve an aliquot of the contaminants into the water 112 — Cooling the mixture to below the melting point to solidify the triglycerides and cannabinoids 114 — Separating the water from the mixture to remove the aliquot of contaminants.

116 — Repeating steps 106-114 to yield a purified lipid solution having less than 20 parts per billion of aflatoxin

FIG. 7 ized as U.S. Pat. No. 9,259,449, which claims priority to
CONCENTRATING CANNABINOIDS IN A LIPID SOLUTION USING MULTI-PHASE PRESSURE CYCLES

CROSS-REFERENCE TO RELATED APPLICATIONS

This patent application is a continuation of co-pending U.S. patent application Ser. No. 15/912,330, filed Mar. 5, 2018, which is a divisional application of U.S. patent application Ser. No. 15/260,607, filed Sep. 9, 2016 issued as U.S. Pat. No. 9,937,219, which is a continuation-in-part of co-pending U.S. patent application Ser. No. 15/043,604, filed on Feb. 14, 2006 issued as U.S. Pat. No. 9,867,859 on Jan. 16, 2018, which is a continuation of U.S. patent application Ser. No. 14/588,150, filed on Dec. 31, 2014 issued as U.S. Pat. No. 9,259,449, which claims priority to U.S. Provisional Patent Application No. 61/964,538, filed on Jan. 7, 2014. The disclosures of each of these patent applications are incorporated herein by reference.

FIELD OF THE INVENTION

This invention relates to ways of concentrating cannabinoids and removing contaminants from concentrated cannabinoids in a lipid extraction process.

BACKGROUND OF THE INVENTION

Cannabinoids are molecules that are detected by cannabinoid receptors in humans and other animals. Endocannabinoids are produced within the human body and function to stimulate the human endocannabinoid system. Phytocannabinoids are produced by plants. There are at least 120 cannabinoids that have been identified. Many of these cannabinoids share the chemical formula $C_{21}H_{30}O_2$. There are various plant sources for phytocannabinoids, including plants from the genus *Cannabis Sativa* L. Hemp is a common term for a variety of *Cannabis Sativa* L. species having less than 0.3% THC according to some regulatory definitions. Hemp is rich in cannabinoids and its extracts are used as medicine.

Other common agricultural crops such as flax are known to produce cannabinoids such as cannabidiol (CBD). CBD is a well known cannabinoid that is used for a variety of purposes including to manage pain and seizures without adverse effects on the user.

Echinacea is a medicinal herb that has been found to contain cannabimimetic N-Alkyamides. N-acylethanoamines are a class of fatty acid compounds which are known to have a significant impact on biological signaling. One of these is anandamide, which is a cannabinoid of interest in many studies.

At least one species of rhododendron has been shown to contain the cannabinoid cannabichromene (CBC). New Zealand liverwort may contain perrottetinenic acid, which is considered to be a cannabinoid very similar in function to trans-Δ9-tetrahydrocannabinol (sometimes referred to herein as tetrahydrocannabinol or THC). The interaction between perrottetinenic acid and the human CB1 receptor and associated health benefits are currently being studied. The breeding and engineering of plants to yield increased levels of perrottetinenic acid is under development.

In some regions of the world, the soils and water are contaminated with naturally occurring and man-made compounds and elements that are toxic to humans. These contaminants include residual pesticides, agricultural fertilizers, naturally occurring microbiological metabolites, and other compounds including toxic minerals and metals.

In recognition of the potential for soil contamination, the State of Washington, in the United States has promulgated maximum concentrations of metals that commercial fertilizers can contain. These are regulated by Washington Administrative Code (WAC) Title 16, Chapter 200. The concentration of these metals allowed in fertilizers sold are shown in Table 1 below.

TABLE 1

Washington Standards For Metals in Fertilizers

| Metals | Lbs./acre/yr. |
|---|---|
| Arsenic (As) | .297 |
| Cadmium (Cd) | .079 |
| Cobalt (Co) | .594 |
| Mercury (Hg) | .019 |
| Molybdenum (Mo) | .079 |
| Nickel (Ni) | .713 |
| Lead (Pb) | 1.981 |
| Selenium (Se) | .055 |
| Zinc (Zn) | 7.329 |

These metals are considered contaminants when found in nutraceutical and food products. While the need for fertilizers is well documented, it is also documented that many plants uptake some of these metals in greater abundance than necessary. Normally, this leads to a balance between agricultural needs and safety. Unfortunately, these contaminant standards were not devised considering that agricultural herbs would play such a prominent role in modem pharmacopeia.

In the United States herbal medicine has become a multi-billion dollar industry. One of the leading herbal medicines is *cannabis*, in its various forms. While there is much focus on Marijuana as a medicine, the Hemp plant is expected to surpass marijuana production as an agricultural and medicinal crop.

Most patients that use of marijuana and hemp for medicinal purposes prefer not to smoke the flower directly, but instead prefer orally consuming a concentrated oil, or edible products made from such oil. A market segment also prefers vaporizing oil as a safer alternative to smoking. The problem is that concentrating herbal and botanical remedies into essential oils also concentrates contaminants, including metals.

There are other sources of contamination of agricultural products, including botanical herbs. Where the plant is not properly cultivated and harvested, mold and other microbial pathogenic organisms may grow on the plant. Microbes may not be harmful by themselves, but they may produce metabolites that function to inhibit competing microbes. The may be produced when the plant grows and after it is harvested.

Aflatoxins, ochratoxins, trichothecenes, zearalenone, fumonisins, deoxynivalenol tremorgenic toxins, ergot alkaloids, and other alkaloids can be toxic to not only to competing microbes, but also to humans, particularly when concentrated. Aflatoxins, particularly Aflatoxin B1, can cause health problems at elevated levels and have been well studied to document levels that are deemed safe.

When botanical extracts including *cannabis* extracts are made, the contaminants in the plant material may be concentrated in the final product.

The American Herbal Products Association (AHPA 2013) has proposed maximum limit for aflatoxin in dried, unprocessed herb products:
Total aflatoxins should be no greater than 20 parts per billion
Aflatoxin B1 should be no greater than 5 parts per billion Heavy Metals Heavy metals are of concern because these elements, and compounds containing these elements, are not typically metabolized by the human body. When heavy metals accumulate in the body, chronic health problems may result. Typical sources of heavy metals include natural processes such as volcanic eruptions and erosion. Human activity including agriculture, mining, refining, an manufacturing also introduce heavy metals into the environment and soil.

*Cannabis*, particularly hemp, has been used for decades in phytoremediation projects worldwide to remove heavy metals from soil. Hemp can tolerate toxic soil and challenging weather conditions and thus, has been used in many places including Chernobyl, Ukraine to remediate soils after a catastrophic nuclear disaster. *Cannabis* has a natural ability to uptake heavy metals from soils, which is good for phytoremdiation projects, but can be problematic when using *cannabis* for food and medicine. While much of these contaminants are restricted to the root structure, some contaminants may be found in the seed, flower and leaf material.

X-ray fluorescence (XRF) is an advantageous way of testing for heavy metal content in *cannabis* because it is portable and does not require heavily processed samples.

There have been various ways to extract and concentrate *cannabis* oils. The removal of contaminants has also been addressed.

U.S. Pat. No. 7,828,966 B2, issued Nov. 9, 2010 to Nakamura discloses a method for purification of botanical oil. The method involves cold-pressing oil and moving the oil through a column having activated carbon. The activated carbon removes contaminants from the oil. Next, the oil is filtered to remove any residual activated carbon micro particles.

U.S. Patent Application No. US 20060167283 A1, filed Sep. 23, 2003, to Flockhart et al. discloses a way of preparing cannabidiol having a purity of 95% or greater. This relies on a solvent such as a C5-C12 straight chain, or branched alkane or carbonate ester of a C1-C12 alcohol. The alcohol solvent enables precipitation of an aliquot of contaminants from the solution of *cannabis* oil. While Flockhart et al. provides an efficient way of purifying cannabidiol, some solvents may leave residual contaminants, and can be expensive to purchase, use and maintain, particularly if not fully recovered post process.

What is desired is a way to minimize contaminants in botanical concentrates such as cannabinoid-containing oil. What is also desired is a cannabinoid containing product that is safe and non-toxic at the recommended dosages. What is also desired is a way of concentrating and purifying phytocannabinoids that is non-toxic, simple, and inexpensive.

SUMMARY OF THE INVENTION

A lipid-based cannabinoid solution is purified using water to remove water soluble contaminants including aflatoxins, metals, pesticides, herbicides and chemical fertilizers from any cannabinoid solution, including any concentrated or extracted cannabinoid solution. Preferably the present invention purifies a lipid-based cannabinoid solution.

The method includes providing a lipid solution including an array of triglycerides, phytocannabinoids and detectable contaminants. The cannabinoids are derived from any cannabinoid containing plant.

The lipid solution is preferably coconut oil. In one embodiment the coconut oil is utilized for the extraction of cannabinoids from plant material such as marijuana (a variety of *Cannabis Sativa* L), hemp, flax, or other cannabinoid containing plant.

Coconut oil contains at least ten triglycerides including medium and long chain triglycerides which collectively have a melting point of approximately 24° C. At the melting point, at least 95% of the coconut oil becomes liquid. It can be appreciated that the melting point can vary depending on the triglyceride mix due to the source of the coconut oil, and manufacturing methods. For example, the melting point of hydrogenated coconut oil is 36-40° C. Preferably the coconut oil is cold pressed and has a melting point of between 22-28° C. so that it solidifies at nearly room temperature.

It can also be appreciated that any plant material is susceptible to some form of contamination, particularly by microbes and metals. The present invention removes contaminants introduced by both the solvent (e.g. coconut oil), and by the cannabinoid containing material.

The cannabinoid solution includes cannabinoids extracted from plant material and it has detectable levels of contaminants. In one embodiment, the water soluble contaminants include at least 20 parts per billion of aflatoxin, or other microbial toxin. The terminology parts per billion (ppb) means the number of µg/kg.

The method dissolves an aliquot of the contaminants into the water. The delivers heat, pressure, agitation, electric charge, a catalyst, or combinations thereof.

The method includes adding water to the lipid solution to create a mixture. It can be appreciated that the more water that is added, the more readily that soluble and semi-soluble contaminants dissolve into the water. Preferably the ratio of water/lipid solution is between 1:1 and 10:1. More preferably the ratio is between 3:1 and 7:1.

In a preferred embodiment, lipid solution has a melting point between 22-28° C. at one atmosphere of pressure. The solution is heated to improve the solubility of many contaminants and to release the contaminants bound by the lipid solution.

After heating, the lipid solution is cooled so that the cannabinoid containing lipids solidify. The solidified lipids separate from the water and float. Cooling is performed at room temperature to reduce manufacturing costs, or may be accomplished with refrigeration.

In a variation of this embodiment, heating is performed in a pressure vessel, such as an autoclave or specially adapted bioreactor, to a temperature above the melting point of the lipid solution. Pressurization and agitation of the mixture accelerates dissolution of the water soluble contaminants into the water. Agitation is accomplished by introduction of jets of purified air, carbon dioxide, other gases, by stirring with a magnetically actuated paddle or other mechanical means. Agitating the mixture includes applying or directing ultrasound to vibrate the mixture.

The step of cooling the mixture causes the triglycerides and cannabinoids to solidify. Cooling is preferably accomplished at room temperature where the melting point of the lipid-solution is above room temperature. In another embodiment, refrigeration expedites the process of cooling.

After cooling the mixture to solidify the lipid-solution, the water is separated from the mixture to remove water soluble contaminants. In one embodiment, an aliquot of the aflatoxin is removed to yield a purified lipid solution having less than 20 parts per billion of aflatoxin. It can be appreciated that the process, or parts thereof, can repeat to achieve the desired reduction of aflatoxin and other water soluble contaminants.

In a variation of the invention the lipid solution is cold-pressed coconut oil, the water is purified water having less than 10 parts per million of dissolved solids, and the step of heating causes the mixture to reach between 22° C.- and 180° C. Preferably, the water is distilled.

In another variation of the invention the method includes ammoniation of the lipid solution, or the mixture, to assure an aflatoxin concentration of less than 20 parts per billion. Amonination includes adding anhydrous ammonia to the water in an amount of 0.5-2% of the water to effectuate ammoniation of the lipid solution or the mixture and thereby assure that aflatoxin B1 concentrations do not exceed 5 parts per billion of the purified lipid solution.

Where heat is used to improve solubility of the contaminants, the step of heating yields a lipid solution temperature of between 22° C.- and 180° C. Where pressure is used, the step of pressurizing includes increasing the pressure of the mixture to above 1 ATM and heating the mixture to above 180° C. Preferably these conditions are maintained for at least ten minutes.

The present invention also includes removing metallic and mineral contaminants from the cannabinoid-containing solution. Preferably heavy metals, which are defined as having a specific gravity of 5.0 or greater are reduced to safe levels.

The method includes extracting *cannabis* into coconut oil having an array of triglycerides, to form a lipid solution having at least 10% cannabinoids, the lipid solution contains at least one heavy metal having a concentration of at least 20 parts per million, the heavy metal having a specific gravity of 5.0 or greater. Distilled water is added to the lipid solution to create a mixture. Electrically charging the mixture achieves electrocoagulation of the mixture, thus enabling an aliquot of the at least one heavy metal to coagulate so that the heavy metal or other contaminant dissolves in the water or precipitates.

Heating the mixture to a temperature above the melting point of the lipid solution and agitating the mixture dissolves soluble contaminants into the mixture and influences the coagulation of the heavy metal. Cooling the mixture causes the triglycerides and cannabinoids to solidify. Separating the water from the mixture to yields a purified lipid solution by removing precipitated and dissolved contaminants. The process or steps thereof can repeat to obtain desired purity of the lipid based cannabinoid solution, i.e. a purified lipid solution containing cannabinoids. The purified lipid solution has less than 10 parts per million of each of: Lead, Uranium, and Arsenic.

The separated water includes dissolved compounds of said at least one heavy metal. The process can remove radioactive contaminants that are found in soil and are found in plant material in trace levels. Preferably, the purified lipid solution has less than 10 parts per million of any contaminant selected from the group consisting of: Arsenic, Aluminum, Cadmium, Cesium, Chromium, Cobalt, Mercury, Molybdenum, Nickel, Iridium, Lead, Osmium, Palladium, Platinum, Plutonium, Radium, Radon, Ruthenium, Rubidium, Selenium, Strontium, Vanadium, and salts and compounds thereof.

The purified lipid solution includes sum of aflatoxins in a concentration of less than 20 parts per billion. The aflatoxin B1 concentration being less than 5 parts per billion.

Agitating the mixture precipitates a portion of the contaminants and the step of separating includes removing the precipitated contaminants.

Electrically charging the mixture is accomplished by introducing highly charged polymeric metal hydroxide species to precipitate contaminants including metals and salts. The metal hydroxide species is presented on charged plates in one embodiment of the invention.

The product is a lipid-based solution including cannabinoids manufactured by any variation of the processes described herein. This yields a purified lipid based cannabinoid oil that can be orally consumed, vaporized, injected, or formulated into a pharmaceutical or nutraceutical compound.

It can be appreciated that the methods and processes of the present invention are useful as a natural water-process to remove contaminants from any cannabinoid containing oil, including lipid solutions containing *cannabis* and concentrated cannabinoid products. It is a natural process that does not use toxic solvents. The contaminants can include various chemical and organic fertilizers, pesticides and herbicides that are commonly applied on plants in an agricultural setting. Such contaminants may be in the soils, water, or directly used on the cannabinoid containing plants used to extract cannabinoids. Many of the residues left by the fertilizers, pesticides and herbicides are by design water soluble, and can be removed by the processes of the present invention.

Accordingly, the process designed to remove metals, minerals and microbial toxins are quite effective at reducing levels of fertilizers, pesticides and herbicides.

BRIEF DESCRIPTION OF THE DRAWINGS

FIG. 1 is a flow chart of a method in accordance with the present invention.

FIG. 2 is a diagram of various pre-processing methods in accordance with the present invention.

FIG. 3 is a flow chart of an extraction method in accordance with the present invention.

FIG. 4 is a diagram of various post-processing methods in accordance with the present invention.

FIG. 5 is a flow chart of a method of post-processing in accordance with the present invention.

FIG. 6 is a flow chart of a method of purifying a lipid-based cannabinoid solution.

FIG. 7 is a flow chart of a method of purifying a lipid-based cannabinoid solution.

FIG. 8 is a system in accordance with the present invention.

FIG. 9 is a system in accordance with the present invention.

DETAILED DESCRIPTION

Extraction Methodology

FIG. 1 is a flow chart of a method 10 of manufacturing a nutraceutical in accordance with the present invention. The method 10 includes the step 12 of pre-processing of plant substrate material to remove a portion of trans-Δ9-tetrahydrocannabinol (THC) from the plant substrate material. The plant substrate material may be any cellulosic component of *cannabis* or other plant that yields cannabinoids.

Cannabinoids are molecules or compounds that stimulate, or cause a reaction in, the endocannabinoid system of the human body. Phytocannabinoids are the subset of cannabinoids derived from plants. The endocannabinoid system (ECS) is a group of endogenous cannabinoid receptors located in the mammalian brain and throughout the central and peripheral nervous systems, consisting of neuromodulatory lipids and their receptors. The CB1 and CB2 receptors are examples of receptors of the endocannabinoid system of the human body. *Cannabis* includes hemp, marijuana, hybrids and genetically modified variants thereof.

In one embodiment, the plant substrate is marijuana, which is pre-processed in accordance with the step 12 to remove superficial cannabinoid-containing plant elements such as tricombs found on the flower and leaves, and which contain the highest concentrations of THC in the plant.

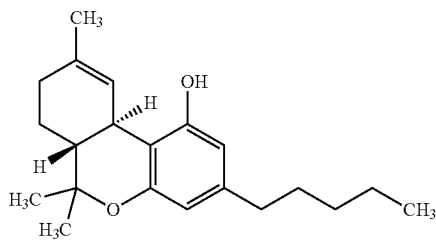

trans-Δ9-Tetrahydrocannabinol (THC)

The method 10 includes the step 14 of extracting cannabinoids. The step 14 can be repeated a number of times until a desired purity and concentration is achieved. The step 14 preferably includes utilizing a multi-stage lipid-based extraction to remove chlorophyll and waxes, and to concentrate cannabinoids. Although a lipid-based extraction technique is preferred, it can be appreciated that numerous known extraction technique can be used. The step 14 yields a virtually full-spectrum extracted cannabinoid mix in a lipid solution.

The method 10 includes the step 16 of post-processing the extracted cannabinoids. The step 16 performs several functions. The first is to volatilize THC and THC-A from the extracted cannabinoids to enable removal of a portion of the THC and THC-A from the extracted cannabinoids. The second function of step 16 is to convert a portion of the THC into CBN. CBD is believed by some to reduce psychoactive effects of THC. In this way the THC content is reduced and the ratio of THC in the cannabinoid mix is decreased. The result is a product that has a higher CBD:THC ratio, reduced psychoactivity and increased attractiveness to consumers in broad markets. Conversion of THC into CBN occurs only significantly when the substrate plant material contains more than 1% THC.

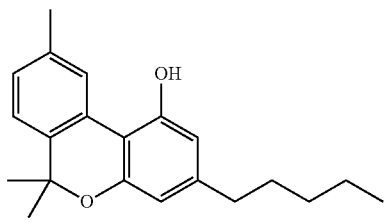

Cannabinol (CBN)

The combination of the step 12 and the step 16 cooperate to reduce psychoactivity of the extracted cannabinoids when used in a nutraceutical or other orally consumable product. The combination of step 12 and step 16 also enables extracted cannabinoids to meet regulatory schemes that require THC content to be within a legally specified limit for nutraceuticals, orally consumed products, suppositories and transdermal products.

The steps 14 and 16 can both achieve decarboxylation of the various acid forms of cannabinoids including Cannabidiol acid (CBD-A), to yield Cannabidiol (CBD), which had improved bioactivity over CBD-A. Together the steps 14 and 16 cooperate to optimize the percentage of cannabinoids that are decarboxylated.

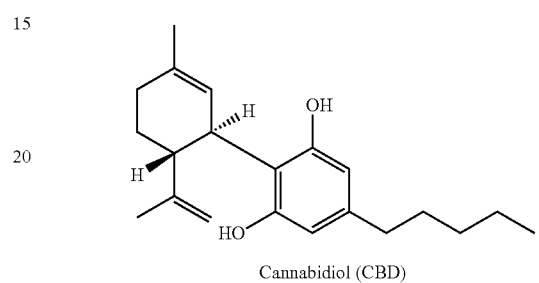

Cannabidiol (CBD)

Figure 2:
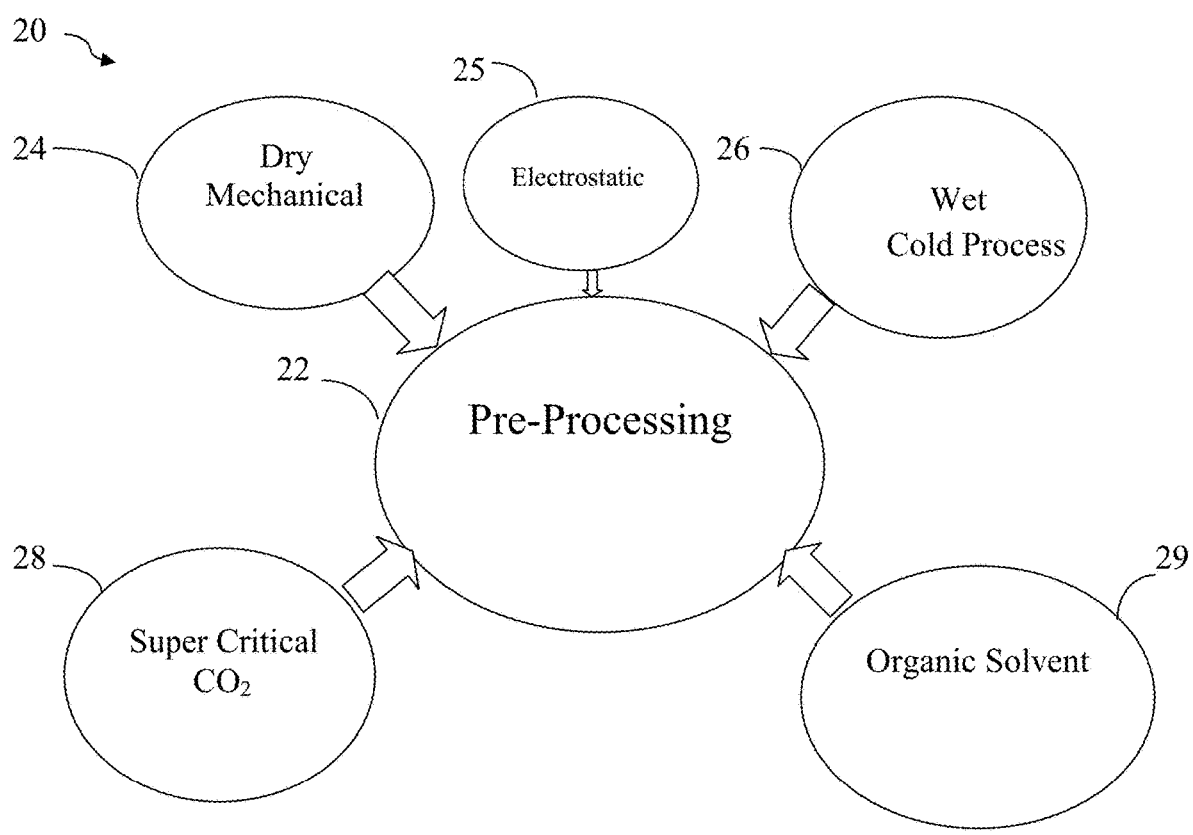

FIG. 2 is a diagram 20 of various pre-processing methodologies in accordance with the present invention. The pre-processing step 22 includes, but is not limited to, at least one step selected from the group consisting of: the step 24 dry mechanical processing, the step 25 of electrostatic processing, the step 26 of wet cold processing, the step 28 of supercritical CO2 extraction, the step 29 of organic solvent extraction, or combinations thereof.

The step 24 of dry mechanical processing includes drying *cannabis*, and mechanically shaking the dried *cannabis* with a sieve shaker having a 150-250 µm sieve openings. Alternatively placing the dried *cannabis* in a centrifuge having a similar sieve opening size achieves the dry mechanical processing of step 24 to rapidly remove tricombs from the flower and leaf material of the dried *cannabis*. Because THC is found in the highest concentrations in the tricombs, this step 24 of dry mechanical processing quickly and efficiently removes a portion of THC from dried *cannabis* material. The dried *cannabis* used herein includes various parts of the *cannabis* plant including leaves and flowers.

The step 25 of electrostatic processing includes passing dry *cannabis* material on a conveyer and feeding it through a thin gap between two parallel planar electrodes of an electrostatic separator. The tricombs are thus separated from the dry *cannabis* material.

The step 26 of a wet cold process includes adding dry *cannabis* to an aqueous solution and cooling, actuation such as shaking or spinning releases tricombs through screens of various sizes to remove the tricombs. The residual *cannabis* plant material is dried for further processing in accordance with the present invention.

The step 28 of super critical CO2 extraction includes applying high pressure CO2 to the dried *cannabis* material to extract a portion of the cannabinoids. While this method is commonly used in the medical marijuana industry and it extracts most cannabinoids from the plant material, it is not 100% efficient. Accordingly, some cannabinoids remain in the substrate material post-extraction. These residual cannabinoids can be recovered by further processing in accordance with the present invention.

Importantly, the present invention can utilize post extraction material that is typically considered waste to achieve a concentrated lipid-based *cannabis* product.

The step 29 of using an organic solvent can include ethyl alcohol extraction of cannabinoids. A rapid extraction using ethyl alcohol will remove tricombs and superficial cannabinoids from plant material, and enable further process steps in accordance with the present invention to further extract and process the residual cannabinoids in the plant material. Again, the present invention can utilize post extraction *cannabis* that is typically considered waste to achieve a lipid-based *cannabis* product.

Various additional solvents used for extraction of cannabinoid also includes propane, butane, and other solvents.

Figure 3:
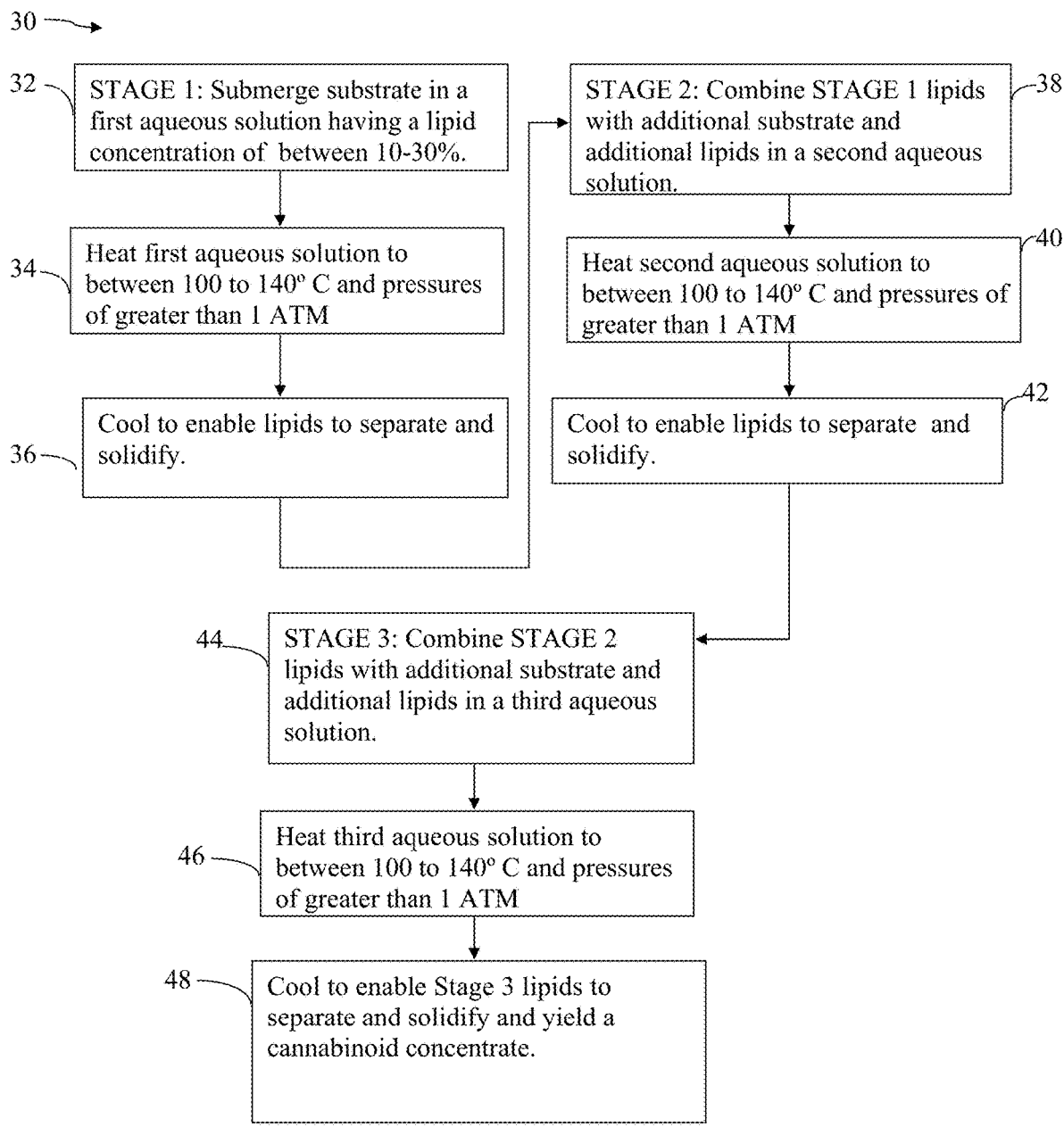

FIG. 3 is a flow chart of an extraction method 30 in accordance with the present invention. The method 30 is a lipid based extraction method that yields a *cannabis* product. An advantage of using a lipid based extraction is that it efficiently extracts cannabinoids residual from *cannabis* plant material that is: post extraction waste, pre-processed in another manner, or unprocessed or dried *cannabis* substrate material. The method 30 can be used to extract cannabinoids from plants other than *cannabis*, including hops.

Another advantage is that the lipid based approach preferably uses organic food grade lipids that are non-toxic. A further advantage of lipid-based extraction is that there is reduced fire or explosion hazard as compared to butane, propane, alcohol and other solvent based extraction techniques. Another advantage of lipid-based extraction over $CO_2$ extraction techniques is that the dangerously high pressures (thousands of psi) associated with $CO_2$ extraction techniques is not required.

The method 30 is a multi stage method. The method 30 preferably includes three stages that commence with step 32, step 38 and step 44, respectively. These extraction stages enable cannabinoids to bond to lipids and inhibit volatilization of cannabinoids by applying pressure at each stage. Multiple stages assures adequate concentrations of cannabinoids in a resulting lipid-based *cannabis* product.

The step 32 begins STAGE 1 and includes submerging substrate in a first aqueous solution having a lipid concentration of between 5-40%. Preferably, the first aqueous solution includes between 5-20% of a lipid-containing oil, such as coconut oil, and 80-95% purified water.

The substrate is preferably dried cannabinoid-containing cellulosic plant material such as leaves or flowers. Cannabinoid-containing plants include *cannabis* and its subspecies and varieties including Hemp, Marijuana, variants, hybrids, and genetic modifications thereof. Cannabinoids are defined substances that effect the CB1 or CB2 receptors in humans. It can be appreciated that cannabinoids can be contained in numerous other plants, including hops. The present invention can be applied to non-*cannabis* plants that contain cannabinoids.

The step 34 heats the first aqueous solution to between 100-140° C. and at pressures of greater than 14.7 psi. Preferably the pressure is between 5-25 psi above atmospheric pressure. Heating the first aqueous solution enables the lipids to bond with the cannabinoids. Pressure makes this process more efficient and inhibits volatilization of various cannabinoids.

The step 36 cools the first aqueous solution to ambient temperature i.e. approximately 22° C. At this temperature the coconut oil solidifies to isolate the STAGE 1 lipids from the water in the first aqueous solution, which are removed to enable STAGE 2.

The step 38 begins STAGE 2, where the STAGE 1 lipids are combined with a second aqueous solution. The second aqueous solution includes a lipid oil having a concentration of between 5-40%. Preferably, the second aqueous solution is between 5-20% of a lipid oil, such as coconut oil, and 80-95% purified water. Additional substrate material is added.

The step 40 heats the second aqueous solution to between 100-140° C. and at pressures of greater than 14.7 psi. Preferably the pressure is between 5-25 psi above atmospheric pressure. Heating the third aqueous solution enables the lipids to bond with the cannabinoids. Pressure makes this process more efficient and inhibits volatilization and escape of various terpenes, diterpenes and other *cannabis* components.

The step 42 cools the second aqueous solution to ambient temperature i.e. approximately 22° C. At this temperature the coconut oil congeals to isolate the STAGE 2 lipids from the water in the second aqueous solution, which are removed to enable STAGE 3.

Step 44 begins STAGE 3 by combining the STAGE 2 lipids with additional lipids and additional substrate in a third aqueous solution including a lipid concentration of between 5-40%. Preferably, the third aqueous solution is between 5-20% of a lipid-containing oil, such as coconut oil, and 80-95% purified water.

The step 46 heats the third aqueous solution to between 100-140° C. and at pressures of greater than 14.7 psi. Preferably the pressure is between 5-25 psi above atmospheric pressure. Heating the third aqueous solution enables the lipids to bond with the cannabinoids.

The step 42 cools the third aqueous solution to ambient temperature i.e. approximately 22° C. At this temperature the coconut oil congeals to isolate the STAGE 3 lipids from the water in the third aqueous solution.

This three stage process provides sufficient purification of cannabinoids to yield a concentrated cannabinoid mix in a lipid solution, where the cannabinoid mix generally matches the cannabinoid mix in the substrate materials used for the method 30 except that a good portion of the acid forms of cannabinoids convert to non-acid forms by decarboxylation.

After each stage mechanical pressure rids much of the aqueous solution from the substrate material. In one embodiment, a vacuum pump is applied to draw residual aqueous solution from the mix of substrate material and aqueous solution prior to cooling the aqueous solution. This assures the maximum amount of cannabinoids are removed from the substrate material.

There are various reasons that the method 30 utilizes coconut oil as the lipid source. Coconut oil is useful because the temperature ranges required for volatilization of THC and conversion of THC to CBN are quite specific and the lipid source needs to be selected to accommodate such temperatures. In particular, temperatures of approximately 132° C. are required to reduce THC to CBN at certain pressures. Coconut oil can endure temperatures of between 177° C. and 204° C. before reaching the smoke point depending on the level of refinement of the coconut oil. Additionally, coconut oil is solid at room temperature i.e. 25° C., which is ideal for separating the cannabinoid infused lipids from an aqueous solution at ambient temperatures. Coconut oil is also a well-known and widely accepted functional food, therapeutic in its own right for various ailments. Consumers that choose nutraceuticals for health purposes tend to also prefer natural and healthy constituents as nutraceutical carriers.

It can be appreciated that various other lipid sources can be used, and that particular lipid sources can be modified or processed to perform within the preferred temperature range requirements of the present invention. For example, Cocobutter oil, canola oil, safflower oil, olive oil, sunflower oil, corn oil, soybean oil, butter, ghee and lard could be substituted for the coconut oil.

The multi-stage extraction process efficiently extracts virtually all cannabinoids from plant substrate material; this process is so efficient that it enables waste plant material that has already been processed into extracts to be used. Accordingly the present invention enables a zero-waste process as an add-on to a facility that performs extractions of cannabinoid substrate materials.

In one embodiment of the invention, where the temperature ranges are reduced through application of a vacuum to volatilize THC and THC-A, the lipid source can be a lipid source having a lower smoke point than coconut oil.

The following is an example of the extraction method 30:

Example 1

Mix 1600 grains of dried *cannabis* substrate (leaves and flowers), ½ gallon of coconut oil, and 4 gallons of water. This yields an approximate ratio of 1:8 lipid oil to water. This ratio produces a concentration of no less than 25 mg of nearly full spectrum extracted cannabinoids per 1 ML of coconut oil. The final extracted oil can then be encapsulated, and taken internally, or applied topically. A capsule could be made of gelatin, plant cellulose, or combined with starch into a pressed pill.

Stage 1:
A. Mix 1600 grams of dried *cannabis*, ½ gallon of coconut oil, and 4 gallons of water is added to the pressure cooker. Heat under pressure at 15 psi at 121° C. degrees for 6 hours.
B. Reduce heat and pressure to 7 psi above atmospheric at 107° C. for an additional 14 hours.
C. The vessel is brought down to atmospheric pressure at 93° C.
D. Saturated substrate is then squeezed of all liquid using mechanical pressure.
E. All liquid is saved and put in a separate stainless steel pot.
F. The stainless pot with liquid is chilled to within 1-10° C. 18 hours to separate water from oil.
G. Remove the solid layer of congealed coconut oil, and place the oil in a separate clean pressure cooker.

Stage 2:
H. Along with the congealed oil that was placed in the clean pressure cooker above, add 1600 grains of dried *cannabis*, and 4 gallons of water. Seal vessel and bring to a 15 psi above atmospheric pressure at 121° C. for 6 hours.
I. The heat source is then set to 7 psi at 107° C. for an additional 14 hours.
J. The vessel is brought down to 0 psi at 93° C.
K. Once at 93° C., saturated substrate material is then squeezed of all liquid using mechanical pressure.
L. All liquid is saved and put in a separate stainless steel pot and chilled to within 1-10° C. 18 hours.
M. After 18 hours, the coconut oil has congealed, separating from the water. At that point, remove the solid layer of congealed coconut oil, and place the oil in a separate clean pressure cooker.

Stage 3:
N. Along with the congealed oil of STAGE 2, add 1600 grams of dried *cannabis,* 4 gallons of water, PLUS an additional 1 liter of fresh coconut oil. Seal vessel and bring to a 15 psi above atmospheric pressure at 121° C. for 6 hours. The additional coconut oil in this stage is added to insure the saturation availability of the entire mixture.
O. The heat source is then set to 7 psi above atmospheric pressure at 107° C. for an additional 14 hours.
P. The vessel is brought down to 0 psi at 93° C. and saturated substrate material is then squeezed of all liquid using mechanical pressure, or with a vacuum.
Q. All liquid is saved and put in a separate stainless steel pot and chilled to within 1-10° C. 18 hours.
R. Remove the solid layer of congealed coconut oil to yield concentrated *cannabis* product in a lipid solution.

Figure 4:
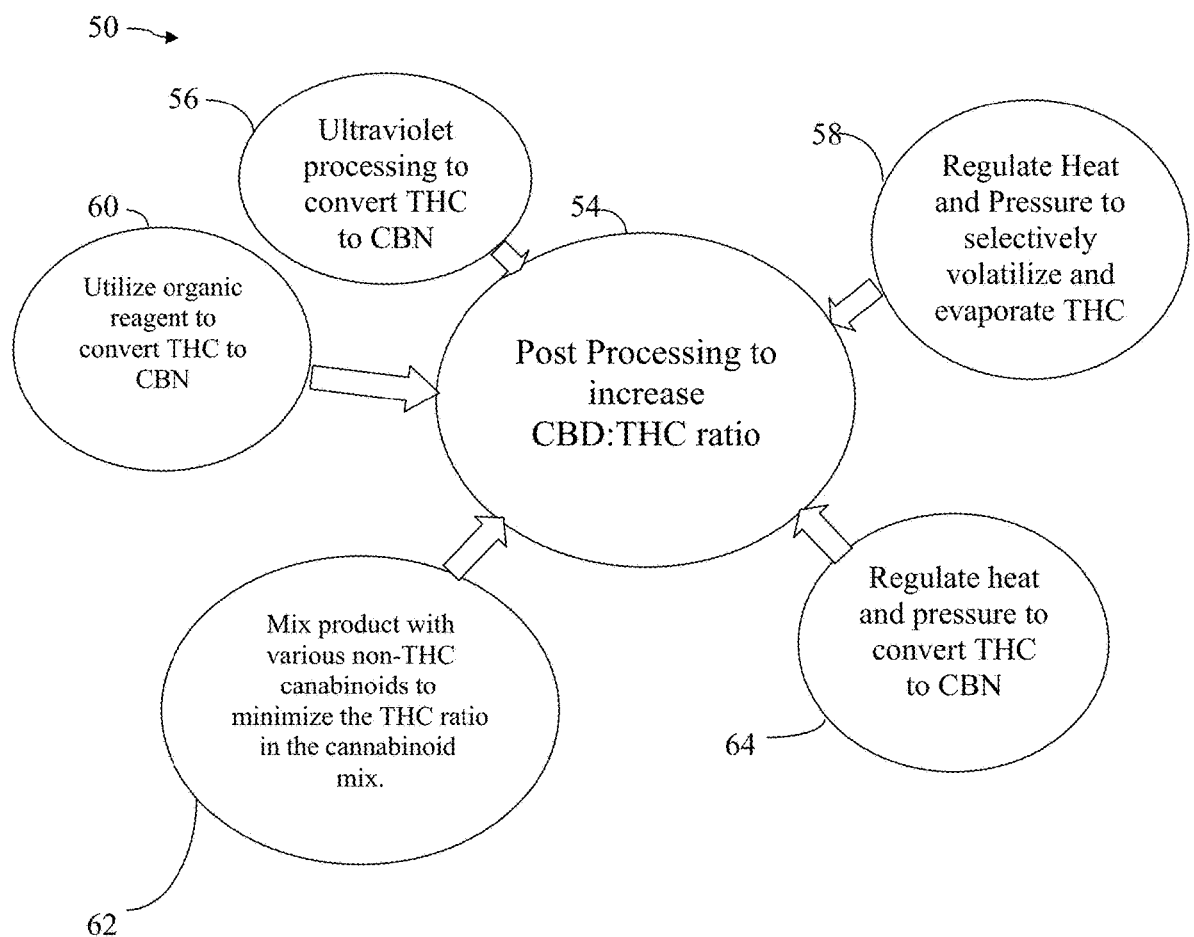

FIG. 4 is a diagram of a post-processing method 50 in accordance with the present invention. The method 50 includes step 54 to increase the CBD:THC ratio of extracted cannabinoids. An example of extracted cannabinoids includes the extracted *cannabis* product in a lipid solution as described above.

The method 50 increases the CBN:THC ratio of extracted cannabinoids utilizing at least one method selected from the group consisting of: the step 56 of directing ultraviolet light through the extracted cannabinoids to convert THC-A and THC to CBN; the step 58 of regulating heat and pressure to selectively volatilize THC-A and THC; the step 60 of utilizing an organic reagent to convert THC to THC-A to CBN; the step 62 of mixing the extracted cannabinoids with various non-THC cannabinoids including CBN to minimize, or reduce, the THC ratio in the cannabinoid mix; and the step 64 of regulating heat and pressure to convert THC to CBN.

The step 58 also regulates humidity, which can influence the vaporization temperature of THC. Preferably the step 58 and 64 are combined and applied to the extracted *cannabis* product to volatilize a first portion of the THC and convert a second portion of THC into CBN. Volatilization (Vaporization) Temperatures at 1 ATM (14.7 psia) of pressure for various cannabinoids is expressed in Table 1:

TABLE 1

| Cannabinoid | Vaporization Temperature ° C. at 14.7 psia (1 ATM) |
|---|---|
| Delta-9-THC | 157 |
| Delta-8-THC | 175-178 |
| CBD | 160-180 |
| CBN | 185 |
| CBC | 220 |
| THCV | 220 |

The vaporization temperature of THC varies considerably with pressure. Table 2 reveals that the present invention can include utilizing a vacuum effectuate volatilization of THC. The term boiling point is used in Table 2 and refers to the volatilization or vaporization point as used herein.

As shown in Table 2, at a temperature of 40° C. and at a pressure of 0.0145 psia, THC will volatilize or boil. Accordingly, in a variation of the present invention, the pressure may be adjusted to remove THC from the extracted cannabinoids at temperatures and pressures expressed in Table 2.

TABLE 2

| % Vacuum | Torr (mm Mercury) | Micron | psia (lb/in$^2$) | Inches Mercury Absolute | Inches Mercury Gauge | kPa abs | Boiling Point delta 9 THC |
|---|---|---|---|---|---|---|---|
| 0.0 | 760.0 | 760,000 | 14.7 | 29.92 | 0.00 | 101.4 | 157C/315F |
| 1.3 | 750.0 | 750,000 | 14.5 | 29.5 | 0.42 | 99.9 | 157C/315F |
| 1.9 | 735.6 | 735,600 | 14.2 | 28.9 | 1.02 | 97.7 | 156C/312.8F |
| 7.9 | 700.0 | 700,000 | 13.5 | 27.6 | 2.32 | 93.5 | 155C/311F |
| 21.0 | 600.0 | 600,000 | 11.6 | 23.6 | 6.32 | 79.9 | 152C/305.6F |
| 34.0 | 500.0 | 500,000 | 9.7 | 19.7 | 10.22 | 66.7 | 148C/298.4F |
| 47.0 | 400.0 | 400,000 | 7.7 | 15.7 | 14.22 | 53.2 | 143C/289.4F |
| 50.0 | 380.0 | 380,000 | 7.3 | 15.0 | 14.92 | 50.8 | 142C/287.6F |
| 61.0 | 300.0 | 300,000 | 5.8 | 11.8 | 18.12 | 40 | 137C/278.6F |
| 74.0 | 200.0 | 200,000 | 3.9 | 7.85 | 22.07 | 26.6 | 128C/262.4F |
| 87.0 | 100.0 | 100,000 | 1.93 | 3.94 | 25.98 | 13.3 | 115C/239F |
| 88.0 | 90.0 | 90,000 | 1.74 | 3.54 | 26.38 | 12 | 113C/235.4F |
| 89.5 | 80.0 | 80,000 | 1.55 | 3.15 | 26.77 | 10.7 | 111C/231.8F |
| 90.8 | 70.0 | 70,000 | 1.35 | 2.76 | 27.16 | 9.3 | 108C/226.4F |
| 92.1 | 60.0 | 60,000 | 1.16 | 2.36 | 27.56 | 8 | 105C/221F |
| 93.0 | 51.7 | 51,700 | 1.00 | 2.03 | 27.89 | 6.9 | 103C/217.4F |
| 93.5 | 50.0 | 50,000 | 0.97 | 1.97 | 27.95 | 6.7 | 102C/215.6F |
| 94.8 | 40.0 | 40,000 | 0.77 | 1.57 | 28.35 | 5.3 | 98C/208.4F |
| 96.1 | 30.0 | 30,000 | 0.58 | 1.18 | 28.74 | 4 | 93C/199.4F |
| 96.6 | 25.4 | 25,400 | 0.49 | 1.00 | 28.92 | 3.4 | 91C/195.8F |
| 97.4 | 20.0 | 20,000 | 0.39 | 0.79 | 29.14 | 2.7 | 87C/188.6F |
| 98.7 | 10.0 | 10,000 | 0.193 | 0.39 | 29.53 | 1.3 | 76C/168.8F |
| 99.0 | 7.6 | 7,600 | 0.147 | 0.30 | 29.62 | 1 | 72C/161.6F |
| 99.9 | 1.0 | 1,000 | 0.01934 | 0.03937 | 29.88 | 0.13 | 44C/111.2F |
| 99.9 | 0.8 | 750 | 0.0145 | 0.0295 | 29.89 | 0.1 | 40C/104F |
| 99.99 | 0.1 | 100 | 0.00193 | 0.00394 | 29.916 | 0.013 | 17C/62.6F |
| 99.999 | 0.0 | 10 | 0.000193 | 0.000394 | 29.9196 | 0.0013 | −5C/23F |
| 100 | 0.0 | 0 | 0 | 0 | 29.920 | 0 | |

Figure 5:
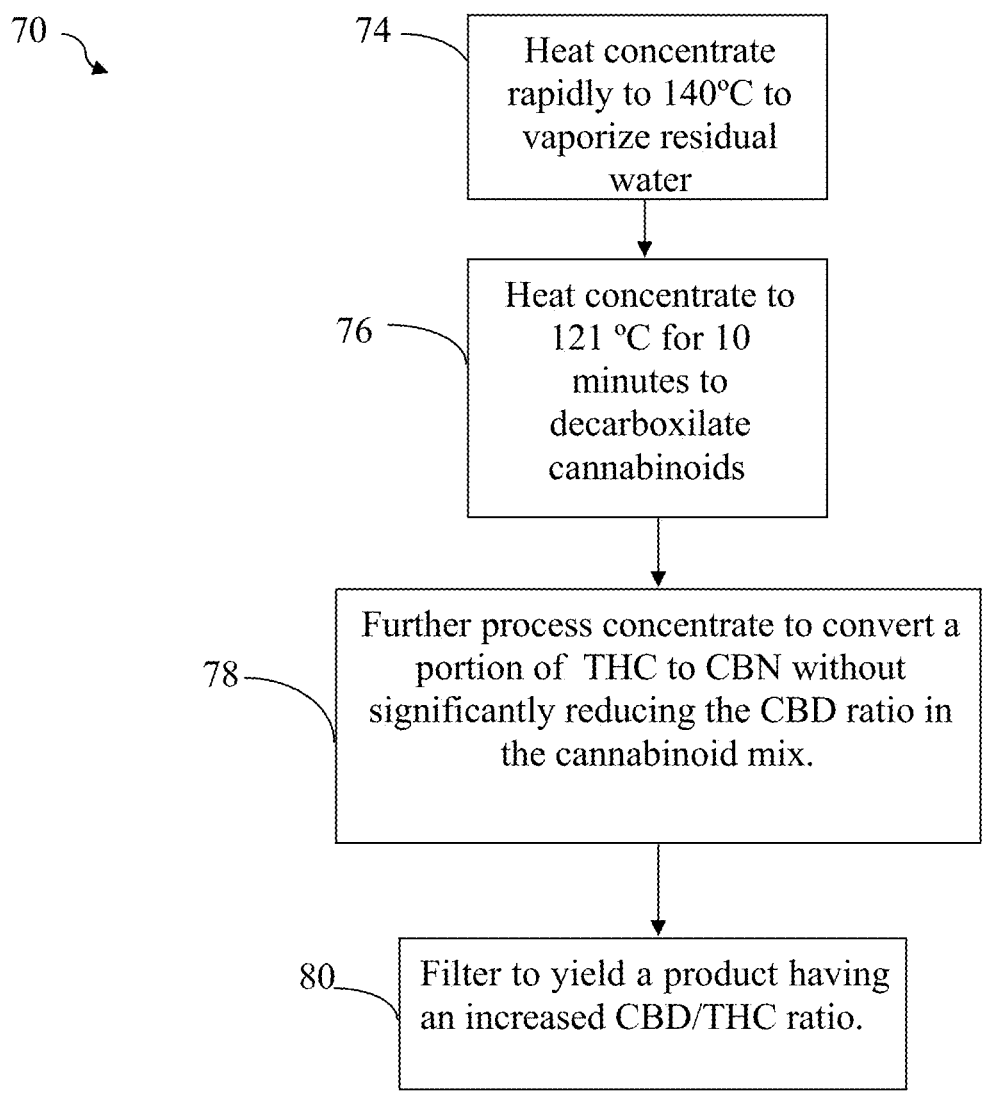

FIG. 5 is a preferred method 70 of post-processing in accordance with the present invention. The method 70 includes the step 74 of heating the extracted *cannabis* product rapidly to at least 140° C. to boil off any residual water in the lipid oil. Further increasing the temperature to the vaporization temperature of THC i.e. 157° C. begins to volatilize the THC. The further increasing of the temperature should not exceed the vaporization temperature of CBD, which is between 160-180° C. The regulation of temperature enables both water and THC to volatilize and evaporate from the lipid oil. The CBD and CBN concentration increase as a percentage in the cannabinoid mix due to the volatilization and evaporation of the THC.

It can be appreciated that temperatures within the range of vaporization of CBD could be utilized in accordance with the present invention, with the advantage of improving the vaporization volume of THC and its isomers, but with the disadvantage of reducing the CBD volume. In a preferred embodiment, a high CBD product is sought so that reducing the CBD content is not preferred. However, in an alternate embodiment where concentrations of various other cannabinoids including CBN, CBC and THCV are sought, then it would be advantageous to increase the temperature to beyond the CBD vaporization temperature.

It can also be appreciated that application of pressure changes the vaporization temperature of various cannabinoids. While it is preferred to utilize the present invention at 1 atm of pressure, it can be appreciated that the present invention can be implemented by changing the pressures and corresponding temperatures, respectively.

The step 76 of heating the concentrate to 121° C. for at least 10 minutes to decarboxylate any remaining non-decarboxilated cannabinoids, the step 78 of further processing the concentrate to convert a portion of THC to CBN without significantly reducing the CBD ratio in the cannabinoid mix, and the step 80 of filtering to yield a product having an increased CBN/THC ratio.

Although some CBD and other cannabinoids may be volatilized or transformed during this process, there will be residual CBD in the cannabinoid mix to achieve a high-CBD and low-THC product, or a THC-free product having no detectable levels of THC.

Test Results

All cannabinoids in their acid forms (those ending in "-A") can be converted to their non-acid forms through a process called decarboxylation when the sample is heated. The molecules lose mass through this process, and thus to find the total theoretical active cannabinoids you must multiply the acid forms by 87.7%. For example, THC-A can be converted to active THC using the formula: THC-A×0.877=THC. The Max THC for the sample is: Max THC=(THC-A×0.877)+THC. This method has been validated according to the principles of the International Conference on Harmonization.

Similarly, CBD-A can be converted to active CBD and the yield is determined using the yield formula: CBD-A×0.877=CBD. Also the maximum amount of CBD yielded, i.e max CBD for the sample is: Max CBD=(CBD-A×0.877)+CBD.

Table 3 below shows the analysis of the cannabinoid mix in a particular Hemp strain sample utilized as a *cannabis* substrate in accordance with the present invention. The sample included only flower material. Often when THC content in hemp strains is determined by government tests, the whole plant is utilized in the test. Here only the flower portion, containing the highest concentration of cannabinoids, is tested. The ratio of max CBD:THC is approximately 22:1 by percentage of the cannabinoid mix.

TABLE 3

| Test | Weight % | Limit |
|---|---|---|
| CBD-V | <0.001% | N/A |
| CBD-A | 21.46% | N/A |
| CBG | <0.001% | N/A |
| CBD | 0.39% | N/A |
| THC-V | <0.001% | N/A |
| CBN | <0.001% | N/A |
| THC | 0.03% | N/A |
| CBC | 0.03% | N/A |
| THC-A | 0.96% | N/A |
| Max THC | 0.88% | N/A |
| Max CBD | 19.21% | N/A |
| Total Active | 0.46% | N/A |
| Total | 22.88% | N/A |

Noteworthy is that there is a max THC of 0.88% and a nearly undetectable amount of CBN percentage on a mass basis of the cannabinoid mix in this substrate sample. The max CBD value is 19.21% which is quite high relative to other medicinal strains of hemp.

Table 4 shows test results for a concentrated cannabinoid product created from the substrate material of Table 3 in accordance with the present invention. Note that the Max THC is 0.14% and the max CBD is 3.81%. Note max CBD equals the CBD value. The max THC equals the THC value. These numbers indicate that full decarboxylation of CBD-A and THC-A has been accomplished. This yields a ratio of max CBD:THC of approximately 27:1 by percentage of the cannabinoid mix.

It can be appreciated that the CBD:THC ratio influences therapeutic efficacy of the product and can be adapted to virtually eliminate psychoactivity of the product. Also, current regulatory framework favors products having a cannabinoid mix having with less than 0.3-0.5% THC, which typically yields a non-psychoactive product. Utilizing a method that does not require laboratory conditions using vacuum distillation or gas chromatography to improve the CBD:THC ratio vastly improves production efficiency while reducing costs.

THC and THC-A are precursors to formation of CBN. The CBN percentage is not detectable because there are undetectably low levels of THC and THC-A presented in the substrate sample reflected in Table 3, and because of the undetectably low levels of CBN originating in the same sample. In alternate embodiments of the present invention, where there are higher levels of THC and THC-A presented in the substrate sample, the CBN percentage would be increased and the CBN:THC ratio in the cannabinoid product would be increased from the ratio detected in the substrate sample.

TABLE 4

| Test | Weight % |
|---|---|
| CBD-V | <0.001% |
| CBD-A | <0.001% |
| CBG | 0.13% |
| CBD | 3.81% |
| THC-V | <0.001% |
| CBN | <0.001% |
| THC | 0.14% |
| CBC | 0.20% |
| THC-A | <0.001% |
| Max THC | 0.14% |
| Max CBD | 3.81% |
| Total Active | 4.28% |
| Total | 4.28% |

Comparing the max CBD:THC ratios shows that the present invention yields an increase in the max CBD:THC ratio from flower substrate sample to the concentrated product. This can accomplished without the need for a vacuum distillation, fractionating columns or a gas chromatography system. The change in the max CBD:THC ratio from the substrate material to the *cannabis* product is a change from approximately 22:1 to 27:1.

When utilizing higher THC content substrate, pre-processing in conjunction with the extraction and post processing yields more dramatic results, and higher concentrations of CBN by weight in the cannabinoid mix. Accordingly, in one aspect of the present invention, a concentrated product having an improved (increased) CBN:THC ratio is achieved by beginning with a substrate having a greater amount of max THC, e.g. between 2%-25% max THC.

A product created in accordance with the present invention yields an improved product having higher CBD:THC ratio and a higher CBN:THC ratio than the substrate material input to the process. Because the material input is non-decarboxilated, the max THC values are determinative of this ratio upon input. Also the max CBD values are similarly determined. The CBN values are selectively determined by varying the substrate, the process time and temperature of the post-process parameters.

The following are examples of the post processing method 50:

Post Processing for Reduction or Elimination of THC

A. After STAGE 3 is complete and the coconut oil congeals and separates from the water, place congealed coconut oil in a clean stainless steel pot. Heat oil rapidly to above 141° C., preferably above the vaporization temperature of THC i.e. 157° C. and below the vaporization temperature of CBD, which is between 160-180° C. This process will remove any remaining water content in the oil and volatilize a portion of THC contained in the concentrated *cannabis* product.
B. Continue heating the oil at 121° C. for an additional 10 min to activate cannabinoids, causing most of any remaining non-decarboxilated portion of the cannabinoids to decarboxilate.
C. Allow the oil to cool to 82° C. and pour through a filter no greater than 20 microns.
D. The oil should be nearly 100% water free and most cannabinoids will be decarboxilated. Concentration of cannabinoids in the cannabinoid product is preferably no less than 25 mg of cannabinoid per 1 ML of coconut oil. E. The oil can then be encapsulated and administered internally or applied topically. A capsule could be made of gelatin, plant cellulose, or combined with starch into a pressed pill.

Example 3

Post Processing to Increase CBD:THC Ratio

A. After STAGE 3 is complete and all oil separated, place congealed coconut oil in a clean stainless steel pot. Heat oil rapidly to above 141° C., preferably above the vaporization temperature of THC i.e. 157° C. and below the vaporization temperature of CBD, which is between 160-180° C. This process will remove the remaining water content in the oil and some THC content will be volatilized. Although some CBD may be volatilized, preferably the *cannabis* substrate used in the various extraction stages is from a hemp strain containing at least a 8:1 ratio of CBD:THC so even with some degradation of CBD, there is a significant residual amount of CBD in the cannabinoid mix.

B. Continue heating the oil at 132° C. for an additional 10 min to convert a portion of THC to CBN.

C. Allow the oil to cool to 82° C. and pour through a filter no greater than 20 microns.

D. The oil should be 100% water free and most cannabinoids will be decarboxilated. The cannabinoid concentration is preferably is not less than 25 mg of cannabinoids per 1 ML of coconut oil.

E. The oil can then be encapsulated and administered internally or applied topically. A capsule could be made of gelatin, plant cellulose, or combined with starch into a pressed pill.

Example 4

Post Processing to Increase CBD:THC Ratio

A. After STAGE 3 is complete and all oil separated, place congealed coconut oil in a clean stainless steel pot. Heat oil rapidly to at least 141° C. This process will remove the remaining water content in the oil.

B. Continue heating the oil at 132° C. for 10-60 minutes to convert a portion of THC to CBN and to volatilize another portion of THC.

C. Allow the oil to cool to 82° C. and pour through a filter no greater than 20 microns.

D. The oil should be 100% water free and most cannabinoids will be decarboxilated. Concentration should be no less than 25 mg of cannabinoid per 1 ML of coconut oil.

E. The final extracted oil can then be encapsulated and administered internally or applied topically. A capsule could be made of gelatin, plant cellulose, or combined with starch into a pressed pill.

Example 5

Post Processing to Increase CBD:THC Ratio

A. After STAGE 3 is complete and all oil separated, place congealed coconut oil in a clean stainless steel pot. Heat oil rapidly to at least 141° C. This process will remove the remaining water content in the oil.

B. Continue heating the oil at 132° C. for an 10-60 minutes to convert a portion of THC to CBN and to volatilize another portion of THC.

C. Allow the oil to cool to 82° C. and pour through a filter no greater than 20 microns.

D. The oil should be 100% water free and most cannabinoids will be decarboxilated. Concentration should be no less than 25 mg of cannabinoid per 1 ML of coconut oil.

E. The final extracted oil can then be subjected to a vacuum and heated to 40° C. at a pressure of 0.0145 psia to remove any residual THC. The extracted oil is then encapsulated and can be administered internally or applied topically. A capsule could be made of gelatin, plant cellulose, or combined with starch into a pressed pill.

While the above paragraphs in this detailed description provide various examples of how a lipid-based cannabinoid oil can be made, it should be appreciated that numerous techniques for making a lipid-based cannabinoid oil can be employed in accordance with the present invention.

Purification of a Lipid-Based Cannabinoid Solution

Figure 6:
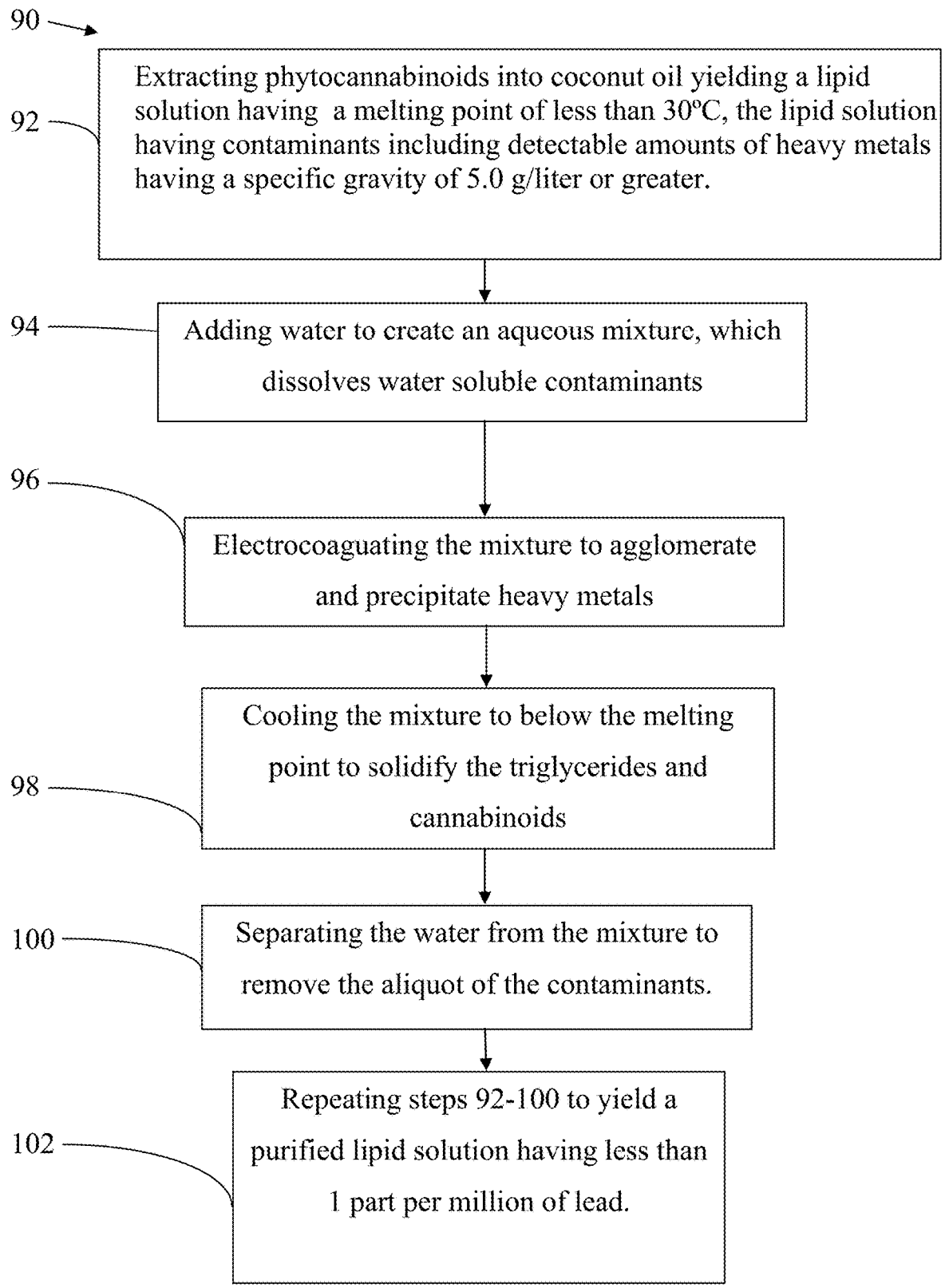

FIG. 6 shows a method in accordance with the present invention, generally designated with the reference numeral 90. The method 90 includes the step 92-102.

The step 92 extracts cannabinoids into coconut oil yielding a lipid solution having a melting point of less than 30° C. The cannabinoids are preferably phytocannabinoids derived from plant material. The lipid solution may have residual contaminants due to cultivation of the plant material. Preferably, the cannabinoids are derived from *cannabis* species such as *Cannabis sativa*, and more preferably from hemp.

In one embodiment, the lipid solution includes detectable amounts of heavy metals having a specific gravity of 5.0 g/liter or greater.

The step 94 includes adding water to create an aqueous mixture. The aqueous mixture dissolves water-soluble contaminants from the lipid solution.

The step 96 electro-coagulates the mixture to agglomerate and precipitate metals, heavy metals, suspended solids, and any other undesirable materials capable of agglomerating under the influence of an electrocoagulation process.

The step 98 cools the mixture to below the melting point to solidify the triglycerides and cannabinoids of the lipid solution. May water-soluble contaminants, suspended solids, and agglomerated metals, are excluded from the solidified lipid solution because they are dissolved, suspended or precipitated in the water.

The step 100 separates the water from the mixture to remove an aliquot of contaminants. This can be as simple as draining the water, or physically manipulating the solidified lipid solution out from the water.

The step 102 includes repeating steps 92-100 to yield a purified lipid solution having safe levels of metals, heavy metals, suspended solids, and any other water-soluble and undesirable contaminants. It can be appreciated that this process removes common chemical fertilizers, herbicides, pesticides, as well as naturally occurring minerals such as arsenic, and metals such as lead, chromium, cadmium, uranium, copper and others.

The electrocoagulation process also removes organic and inorganic colloids that are held in solution by electrical charges. Coagulation introduces ions having electrical charges that destabilized the colloids allowing them to coagulate. A charged ion species which is metallic or otherwise is introduced into the solution in the form of a plate, rod, screen or other matrix. Preferably the electrocoagulation system would include pairs of conductive metal plates in parallel to function as monopolar sacrificial electrodes.

While most electrocoagulation processes are typically not optimized to remove super soluble materials including calcium and magnesium ions, which are not easily disassociated from an aqueous solution, these super soluble ions are readily removed when the water is separated from the solidified lipid solution. Eectrocoagulation utilizing a graphene membrane can optimize removal of these super soluble materials.

In sum, the present invention is adept at removing supersoluble, soluble and insoluble contaminants from a lipid-based *cannabis* solution.

FIG. 7 shows a method of creating a purified cannabinoid solution generally designated 104 in accordance with the present invention. The method 104 includes steps 106 through 116.

The step 106 includes providing a cannabinoid solution including triglycerides, cannabinoids, trace levels of contaminants. The cannabinoid solution is preferably an extract of *cannabis* having undetectable amounts of THC and therapeutic amounts of CBD. More preferably the cannabinoids solution is derived from hemp. The cannabinoids solution has a melting point of less than 40° C. and more preferably less than 27° C., and yet more preferably less than 25° C. so that the cannabinoids solution will solidify at nearly or at room temperature. It can be appreciated that the cannabinoid solution can be derived from non-*cannabis* cannabinoids.

The step 108 includes adding purified water to create an aqueous mixture. Preferably the purified water is distilled water having less than 10 parts per million (ppm) of suspended solids. Alternatively the purified water is filtered through reverse osmosis or other way of purifying water.

The step 110 includes heating the mixture in a pressure vessel to above the melting point of the cannabinoid solution. Further the mixture is pressurized beyond one atmosphere of pressure and agitated. The pressure in combination with temperature optimization and agitation optimizes the solubility of these contaminants and enables the dissolution of an aliquot of the contaminants into the water. As a result a significant amount of water-soluble contaminants are readily removable from the cannabinoid solution by separation of the cannabinoids and water.

The pressure in combination with temperature optimization and agitation suspends various solids in the water through the combined action of agitation, pressurization, and optimization of solution temperature. The combination of eliminated suspended solids, and improving solubility, purifies the cannabinoids when the water is separated from the cannabinoids.

The step 112 cools the mixture to below the melting point of the lipid-based cannabinoid solution to solidify the triglycerides and cannabinoids. In this embodiment, the step 114 separates the water from the mixture to remove the suspended and dissolved solids including the aliquot of contaminants. The step 116 repeats steps 106-114 to yield a purified lipid solution having safe levels of aflatoxin and other contaminants. Preferably, the total aflatoxin levels are less than 20 parts per billion and the levels of aflatoxin B1 are below 5 parts per billion. More preferably, no detectable amount of aflatoxin is in the purified lipid solution.

It can be appreciated that various alternate ways can separate water from the cannabinoid solution including filtering, centrifugal separation and other known methods.

Figure 8:
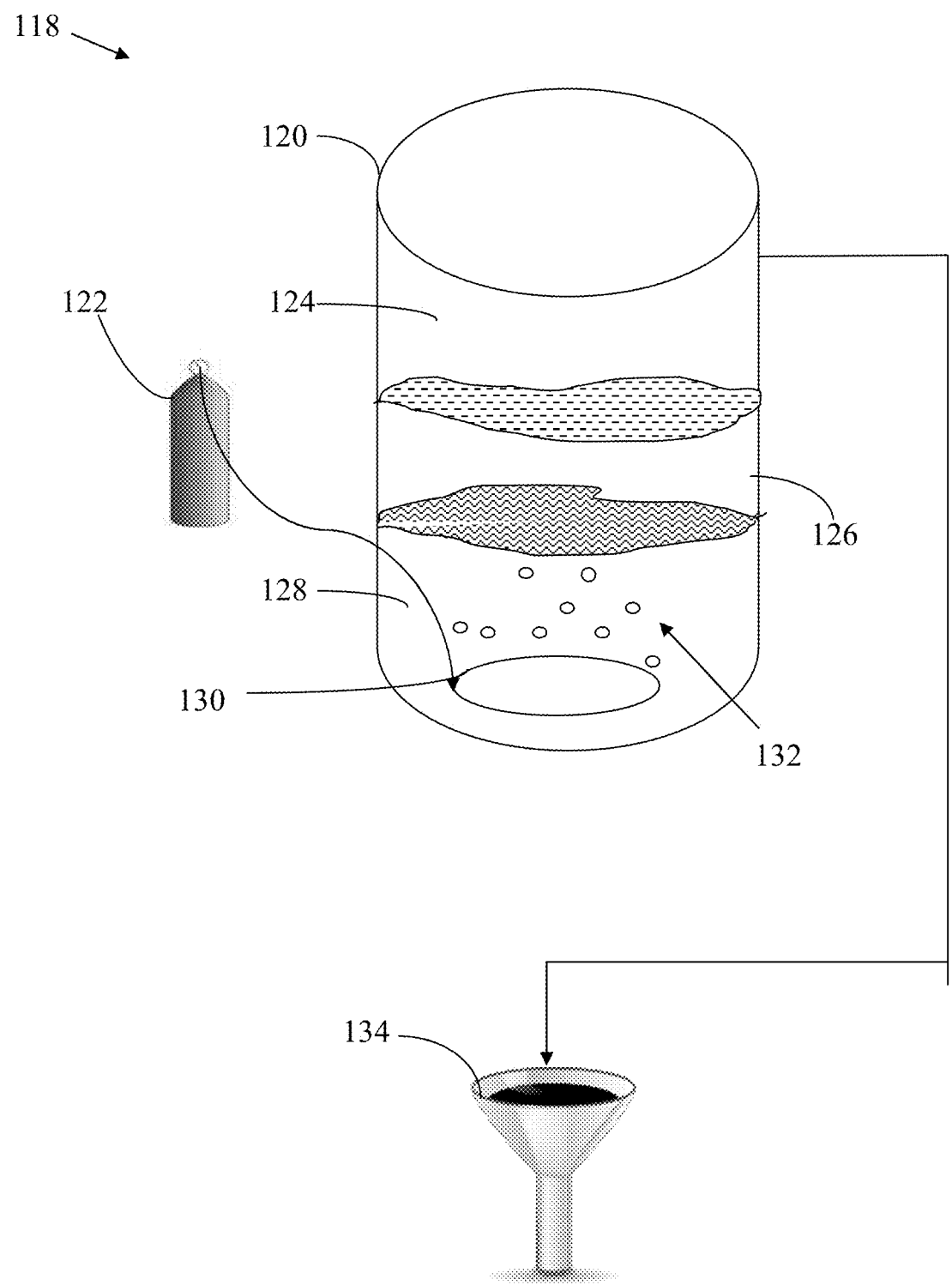

FIG. 8 is an exemplary system in accordance with the present invention generally designated with the reference numeral 118. The system 118 includes a vessel 120, a carbon dioxide tank 122 with gaseous $CO_2$, a $CO_2$ bubbler 130, and a filter 134. The tank 122 delivers pressurized $CO_2$ to the bubbler 130 to force gaseous $CO_2$ into the vessel 120.

In operation the vessel 120 is filled with water 128, substrate material 126 and ice 124. The substrate material 126 is generally suspended or floating in the water 128 and the ice 124 floats on the substrate material 126. Thus three layers are formed. Release of the $CO_2$ into the water via the bubbler 130 agitates the contents of the vessel 120 for twenty to sixty minutes in one embodiment of the invention. Agitation creates a slurry of water, ice and substrate material. In one embodiment the substrate material is a cellulosic plant material such as *cannabis* leaves and flowers.

The contents of the vessel 120 are agitated at near freezing temperatures i.e. between 0-10° C., the contents form a slurry of water, ice and substrate material. Plant trichomes, which comprise crystallized cannabinoids, float to the surface to form a trichome mixture in a distinct layer. The trichomes include Bulbous, capitate-sessile, and capitate-stalked trichomes.

The trichome mixture is separated from the slurry and filtered, for example through a 220-245 micron filter, then the trichome mixture is passed through a 45 micron filter to yield a concentrated cannabinoid product.

While the cold process achieved by the system 118 yields a concentrated cannabinoid product including cannabinoids lipids and waxes, the temperature range used may not yield the purest possible product and some water soluble contaminants may still be present.

Figure 9:
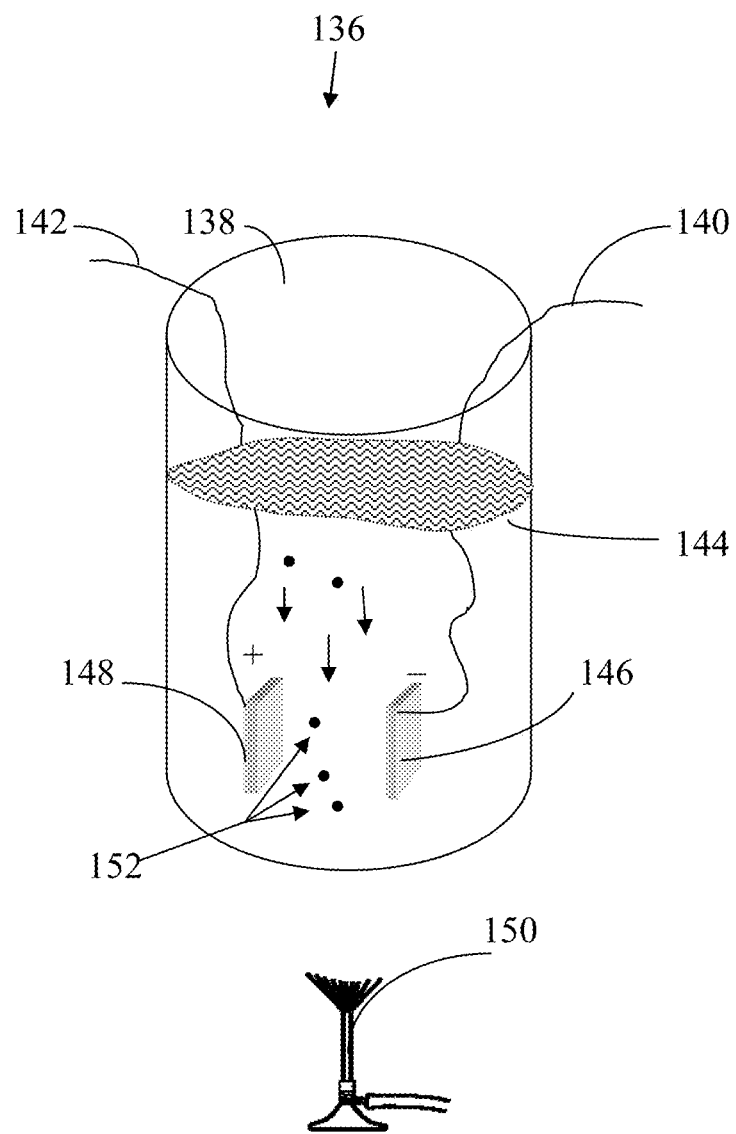

FIG. 9 shows a system utilized in accordance with the present invention, generally designated with the reference numeral 136. The system 136 effectuates electrocoagulation of a cannabinoid solution 144, including but not limited to, a cannabinoid solution produced by the system of FIG. 8.

The system 136 includes a container 138, a DC voltage source positive wire 142 and a DC voltage source negative wire 140. The positive wire 142 connects to an anode plate 148 of conductive material and the negative wire 140 connects to a cathode plate 146 of conductive material. The cannabinoid solution 144 contains an added electrolyte in one embodiment of the invention. Flowing DC current through the cannabinoid solution 144 causes metal ions to change into metal oxides, and also causes agglomeration of suspended solid contaminants. The agglomerated contaminants 152 precipitate and can be filtered with an 11 micron filter, for example. This yields a purified cannabinoid solution with particles of 10 microns or less. Further filtration is enabled.

In a preferred embodiment the system 136 includes a heat source 150 to improve solubility of the contaminants in the cannabinoid solution 144. As a result an aliquot of contaminants are dissolved from lipids in the cannabinoid solution into the water contained in the cannabinoid solution. In this way, electrocoagulation achieves improved efficiency over an ambient temperature system.

The anode 148 and cathode 146 are a metallic conductor such as iron, copper, aluminum or stainless steel. More preferably numerous plates are aligned with a small gap i.e. between 1 mm-10 mm between the plates. The plates alternate between anode and cathode charges. The voltage difference between the adjacent plates is between 1-10 volts. In one embodiment 0.25-4 amps of current is used.

In an alternate embodiment, the system 136 includes plates having a copper foil substrate coated with graphene to optimize the electrocoagulation process.

In yet another embodiment, the system includes an outer anode plate 148 and an outer cathode plate 146 with numerous uncharged plates positioned there between. The uncharged plates are preferably made with graphene to enable protons to flow unimpeded through the uncharged plates resulting in a cannabinoid solution having a highly ionic character to improve electrocoagulation.

In yet another embodiment, the anode 148 and cathode 146 plates are formed into a cylindrical shape with one nested within the other. This yields a greater conductive surface area for any given volume of the system.

In yet another embodiment, the system includes graphene membranes having graphene-containing tubes formed in axial alignment to form a plate or membrane. An advantage of graphene is that metal from a sacrificial anode does not add contaminates the *cannabis* solution.

Preferably the heat source 150 brings the temperature of the cannabinoid solution 144 to between 50-100° C. to improve solubility of any water soluble contaminants contained therein. Such contaminants are removed by electrocoagulation. After electrocoagulation is effectuated, the cannabinoid solution 144 is filtered and cooled to enable the lipids contained in the cannabinoid solution to solidify. In one embodiment, the lipids include the waxes and other lipids naturally included in the *cannabis* plant. In another embodiment, a plant lipid mix is added from coconut oil, or olive oil for example.

Upon solidification of the lipids they are separated and removed from the cannabinoid solution to yield a purified lipid solution. The purified lipid solution is dehydrated in an over at between 50-75° C. in one embodiment of the invention.

While various embodiments and examples of the present invention are discussed, there are many variants of the inventive concept that constitute the present invention. Accordingly, the invention is to be limited only by the appended claims.

I claim:

1. A process for using a pressure vessel to purify and concentrate a coconut oil/cannabis sativa solution, comprising:

a. providing a coconut oil and *cannabis sativa* solution, wherein the melting point of the coconut oil/*cannabis sativa* solution is between 22° C.-28° C. at one atmosphere of pressure;
b. adding water to the coconut oil/*cannabis sativa* solution to create a mixture;
c. providing a pressure vessel and pressurizing the mixture in the pressure vessel in a first phase where the pressure reaches between 5 psi-25 psi above atmospheric pressure;
d. pressurizing the mixture in the pressure vessel in a second phase where the pressure reaches 15 psi above atmospheric pressure at a temperature of 100° C.-180° C. for 6 hours;
e. cooling the mixture to below the melting point of the coconut oil/*cannabis sativa* solution to cause the triglycerices and tetrahydrocannabinol to solidify;
f. agitating the mixture prior to separating out the water; and
g. separating out the water from the mixture to yield a concentrated coconut oil/*cannabis sativa* solution having a tetrahydrocannabinol content of at least 1 mg/ml and removing the solidified coconut oil/*cannabis sativa* lipids from the precipitated contaminants and *cannabis sativa* to yield a purified and concentrated coconut oil/*cannabis sativa* solution.

* * * * *